United States Patent [19]
Chondroudis et al.

[11] Patent Number: 6,150,536
[45] Date of Patent: Nov. 21, 2000

[54] DYE DOPED ORGANIC-INORGANIC HYBRID MATERIALS

[75] Inventors: Konstantinos Chondroudis, North White Plains; David Brian Mitzi, Westchester, both of N.Y.

[73] Assignee: International Business Machines Corporation, Armonk, N.Y.

[21] Appl. No.: 09/350,429

[22] Filed: Jul. 8, 1999

[51] Int. Cl.$^7$ ............................... C07F 7/24; B32B 7/02; C07D 413/00

[52] U.S. Cl. ................................ 549/2; 549/27; 549/42; 549/206; 549/399; 548/101; 548/215; 548/240; 556/81; 556/400; 428/212; 117/68; 117/940

[58] Field of Search ................... 556/81, 400; 428/212; 117/68, 940; 549/2, 42, 27, 206, 399; 548/101, 215, 240

[56] References Cited

U.S. PATENT DOCUMENTS

| | | | |
|---|---|---|---|
| 5,783,292 | 7/1998 | Tokito et al. | 428/212 |
| 5,871,579 | 2/1999 | Liang et al. | 117/68 |

OTHER PUBLICATIONS

"Synthesis, Structure and Properties of Organic–Inorganic Perovskites and Related Materials" D. Mitzi, Progress in Inorganic Chemistry, V48, edited by K Karlin, pp. 1.2,89–95 (1999).

"Enhanced Phosphorescence from Napthalene–Chromophore Incorporated into Lead Bromide–based layered Perovskite . . . " Era et al., Chem Phys Lett. 296 (1998) 417–420.

"PbBr–Based Layered Perovskite Containing Chromophore–Linked Ammonium Molecule as an Organic Layer" Era et al. Chem Lett. (1997) pp. 1235–1236.

Appl. Phys. Lett. 65 (6), Aug. 8, 1994, pp. 676–677, M. Era et al., "Organic–Inorganic Heterostructure Electroluminescent Device Using a Layered Perovskite Semiconductor $(C_6H_5C_2H_4NH_3)_2PbI_4_2$".

*Primary Examiner*—Porfirio Nazario-Gonzalez
*Attorney, Agent, or Firm*—Ohlandt, Greeley, Ruggiero & Perle, L.L.P.

[57] ABSTRACT

The present invention relates to an organic-inorganic hybrid material comprising an organic component and an inorganic component. The organic component comprises a dye that fluoresces in the visible range. In addition, an optically inert component may replace a portion of the organic dye component to increase fluorescence.

14 Claims, 5 Drawing Sheets

DYE DOPED ORGANIC-INORGANIC HYBRID MATERIALS

FIELD OF THE INVENTION

This invention relates to the field of organic-inorganic hybrid materials. More particularly, it relates to luminescent hybrid materials that may be used in electroluminescent devices.

BACKGROUND OF THE INVENTION

Organic-inorganic hybrids are a technologically important class of materials, offering the possibility of combining useful properties of both organic and inorganic components within a single molecular composite. Optical and electrical properties of organic materials, for example, can be tuned relatively easily by modifying their molecular structure. Their ease of processing, plasticity, and low price make organic materials attractive for a number of applications. Lack of robustness, thermal stability, and low electrical mobility, however, inhibit their use in many of the same applications. These latter properties are offered by inorganic materials. By synthesizing organic-inorganic composites, the best of both worlds can potentially be obtained within a single material.

The layered organic-inorganic perovskites are a subclass of the organic-inorganic hybrids, and have recently attracted substantial interest due to their potential for unique electrical, magnetic and optical properties. The basic building component of this family is the inorganic $ABX_3$ perovskite structure. By replacing the A inorganic cation with an organic one, organic-inorganic hybrid perovskite compounds are formed. In these ionic compounds the organic component is an intimate part of the structure since the structure actually depends on the organic component for charge neutrality. Therefore, the compounds exhibit specific stoichiometries. The layered (two-dimensional) $A_2BX_4$, $ABX_4$ and the one-dimensional $A_3BX_5$, and $A_2A'BX_5$ perovskites also exist and are considered derivatives of the three-dimensional parent family.

In these lower dimensionality compounds, exciton formation is observed within the inorganic sheets, with large binding energies (>300 meV) and oscillator strength. Interesting physical properties such as strong room temperature photoluminescence, third harmonic generation, and polariton absorption arise from these excitons. The strong photoluminescence and the ability to tune the emission wavelength by means of incorporating different metal or halogen atoms in the structure make these perovskites attractive as emitter materials in electroluminescent devices, although currently such devices operate only at low temperature. Generally, simple organic cations such as aliphatic or single ring aromatic ammonium cations are used to form these structures. These cations are optically and electrically inert.

It is an object of the present invention to provide an organic-inorganic hybrid that incorporates a mixture of functional, optically active, luminescent dye molecules and optically inert molecules within the organic component of the structure. The dilution of the dye molecule within the organic component will reduce self-quenching interactions occurring between the dye molecules, which in turn will increase the luminescence yield.

It is another object of the present invention to provide an organic-inorganic material that is not random, but rather self assembles itself into a predictable arrangement of organic and inorganic components. This reduces the variability of luminescence and increases charge conduction between the inorganic and organic components.

It is a further object of the present invention to provide an organic-inorganic material that is readily deposited on a substrate by simple and inexpensive methods.

SUMMARY OF THE INVENTION

The present invention relates to an organic-inorganic hybrid material including an organic component and an inorganic component. The organic component comprises a dye that luminesces in the visible range. In addition, an optically inert component can replace a portion of the organic dye component, resulting in an organic-inorganic hybrid material that has a higher intensity luminescence than a hybrid material that is fully loaded with the organic dye.

DETAILED DESCRIPTION OF THE INVENTION

Figure 1:
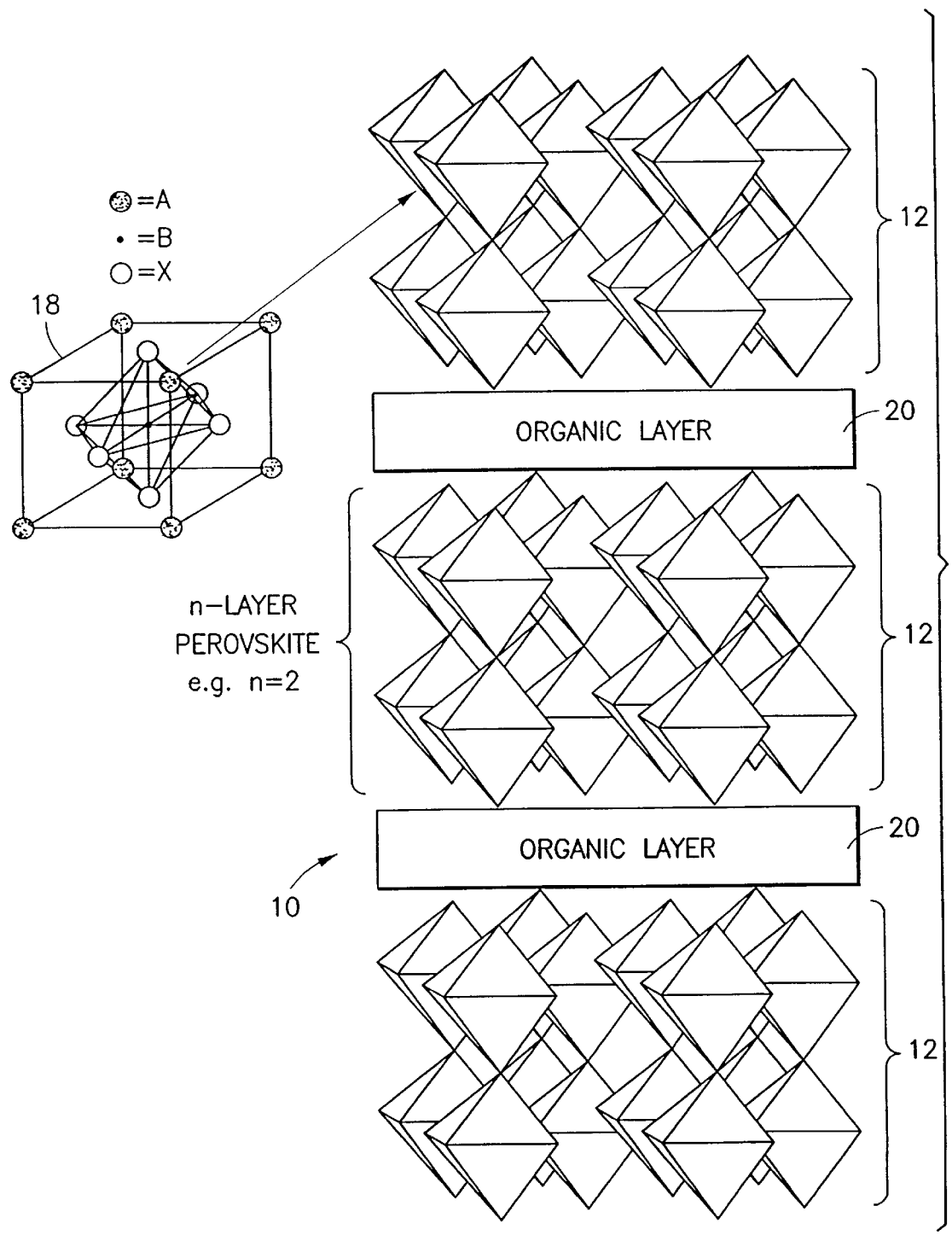
FIG. 1 illustrates an example of an organic-inorganic hybrid material that is based on a three-dimensional perovskite structure, $ABX_3$.

The present invention relates to an organic-inorganic hybrid material containing a dye that luminesces in the visible range.

The organic-inorganic hybrid material of the present invention combines the advantages of an inorganic crystalline material with those of an organic material. The organic component comprises a dye component and an optically inert component that facilitates the self-assembly of the organic-inorganic hybrid material into a crystalline like structure. The inorganic component forms an extended one-, two- or three-dimensional network that provides the high carrier mobility characteristic of inorganic crystalline solids. The excitons associated with these inorganic networks may be transferred to the organic dye, increasing its emission, especially when the dye is tailored to absorb in the wavelength range of the exciton.

In addition, by incorporating an optically inert component (that does not absorb or luminesces in the visible range) the luminescence is further enhanced due to a reduction of the self-quenching interactions between the dye molecules. A subclass of luminescence is fluorescence (emission arises from allowed transitions, involving singlet excited states and requiring less than $10^{-7}$ to occur). By using fluorescent organic molecules these improvements can provide for an efficient emission layer if these materials are used in the fabrication of organic light emitting diodes.

For the purposes of this invention, an organic-inorganic hybrid material shall mean a material composed of: organic components and inorganic components which are mixed together on a molecular level, and (i) wherein the material is characterized by a substantially fixed ratio of each organic component to each inorganic component; and (ii) wherein both organic and inorganic components manifest forces that enable a self assembly therebetween into a predictable arrangement.

One example of an organic-inorganic hybrid material takes the form of an organic-inorganic perovskite structure. Layered perovskites naturally form a quantum well structure in which a two dimensional semiconductor layer of corner sharing metal halide octahedra and an organic layer are alternately stacked.

For preparation of such organic-inorganic hybrid materials, spin-coating techniques are suitable because many organic-inorganic perovskites are soluble in conventional aqueous or organic solvents. Using this method, high quality, highly oriented, layered perovskite thin films have been achieved. Vacuum evaporation techniques have also been used to grow films of layered perovskites. Copending U.S. patent applications Ser. No. 09/192,130, entitled "Single-Source Thermal Ablation Method for Depositing Organic-Inorganic Hybrid Films"; and U.S. Pat. No. 5,871,579, entitled "Two-Step Dipping Technique for the Preparation of Organic-Inorganic Perovskite Thin Films", are assigned to the same Assignee as this Application. Both documents teach alternative deposition methods for organic-inorganic hybrid materials. The disclosure of the aforementioned documents is incorporated herein by reference.

FIG. 1 illustrates one example of an organic-inorganic hybrid material 10 that is based on a three-dimensional perovskite structure, $ABX_3$. The perovskite structure comprises corner-sharing $BX_6$ octahedra 12. Each octahedron 12 is defined by six X anions at the vertices and one B cation in the center (see crystal schematic 18). The A cations sit in the large interstices between octahedra 12.

Layered inorganic compounds based on the three dimensional perovskite structure can be visualized by taking an n-layer thick "cut" (n=1 to infinity) along the <100> or <110> planes of the perovskite. In the organic-inorganic hybrid materials, the anionic, inorganic $BX_6$ octahedra of the perovskite sheets are charge balanced by cationic, organic molecules 20 forming alternating layers and/or sitting in the A cation interstitial sites. Examples of these materials include B=Group 14 (IV A), transition metal, and rare-earth elements, X=halogen (Cl, Br, or I), and A=organic ammonium or diammonium cations. In the present invention, the organic ammonium or diammonium cation is a mixture of a dye derivative that will luminesce in the visible range and an optically inert material.

Inorganic perovskite sheets 12 and organic layers 20 are bound by strong, ionic and hydrogen bonding. The ionic bonding requires the organic-inorganic compound to have a specific stoichiometry and the organic molecules to sit in well-defined, crystallographic sites. The bonding between the organic and inorganic layers causes these hybrid materials to deposit as locally-ordered or crystalline, thin films or to grow as single crystals.

Figure 2:
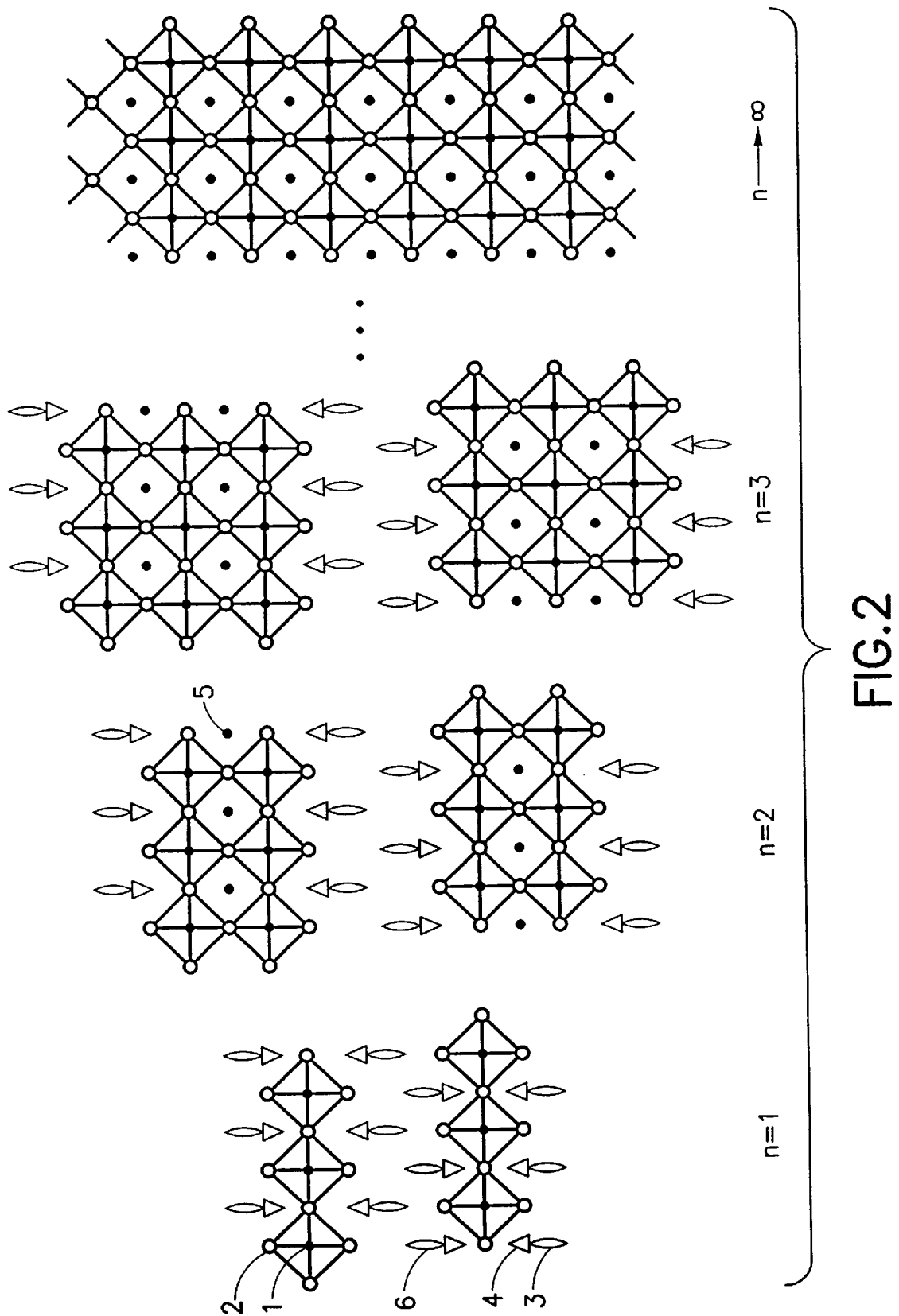
FIG. 2 illustrates a preferred perovskite structure with the general formula: $(RNH_3)_2(CH_3NH_3)_{n-1}M_nX_{3n-1}$.

A preferred perovskite material shown in FIG. 2 has the general formula: $(RNH_3)_2(CH_3NH_3)_{n-1}M_nX_{3n+1}$, wherein R is an organic group; M is a divalent metal, X is a halogen and n is one or more. Metal atom 1 is a divalent metal able to adopt an octahedral coordination. Organic component 6 is composed of two components: ammonium cation 4 and organic group 3. The ammonium cation 4 hydrogen bonds to the inorganic halogens 2, with organic group 3 extending into the space between the layers and holding the structure together via van der Waals interactions.

Figure 3:
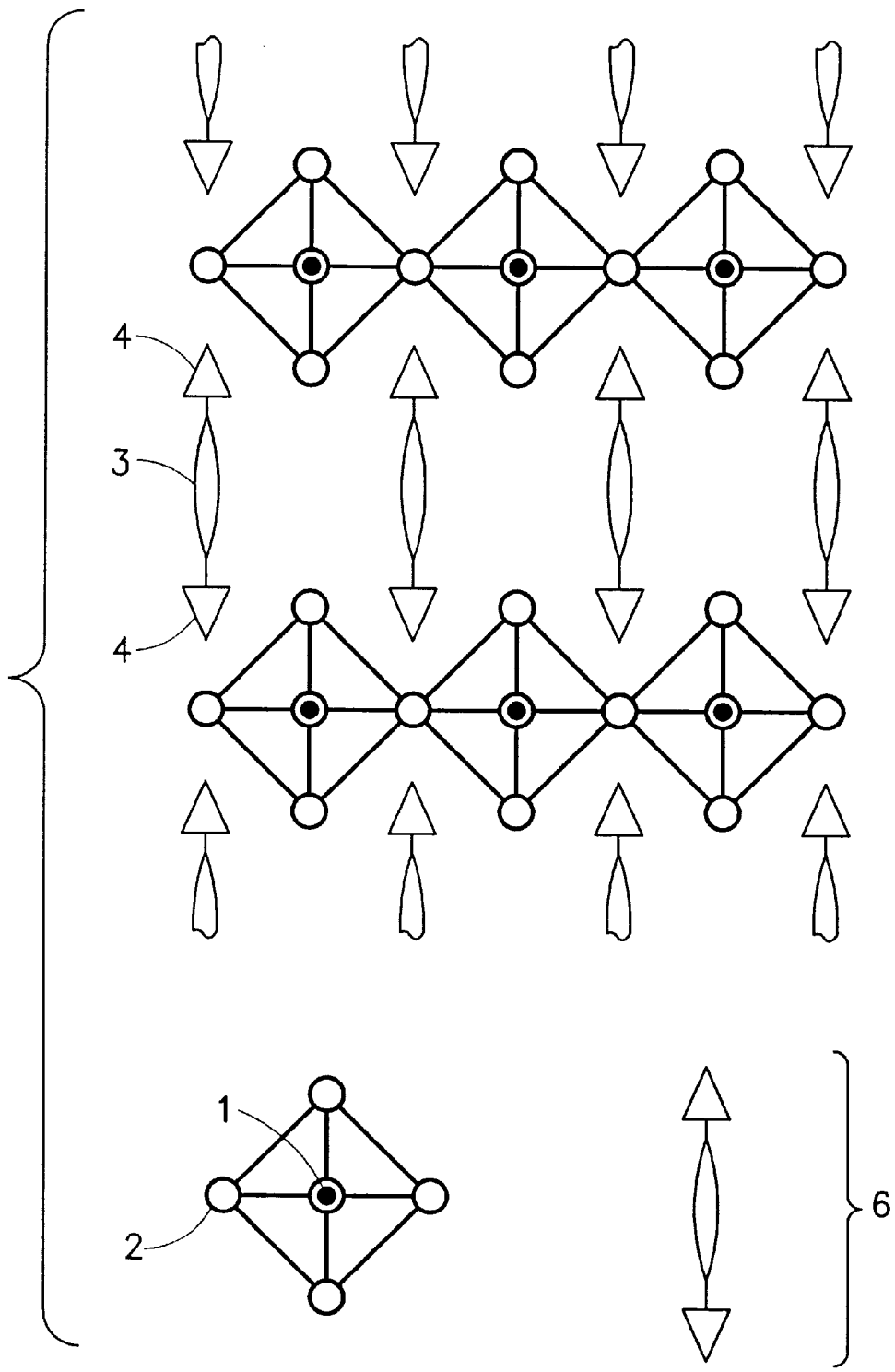
FIG. 3 illustrates a preferred perovskite structure with the general formula: $(NH_3-R-NH_3)(CH_3NH_3)_{n-1}M_nX_{3n-1}$, wherein n=1.

Another preferred perovskite contains a diammonium cation having the general formula $(NH_3—R—NH_3)$ $(CH_3NH_3)_{n-1}M_nX_{3n+1}$, where R, M, X, and n are described above. FIG. 3 illustrates the diammonium cation perovskite structure when n=1. In this case, organic component 6 has two ammonium cations 4 that bond to the inorganic halogens 2.

The organic component is preferably a derivative of a dye that will fluoresce in the visible range. Examples of preferred dye derivatives are tolan, thioxanthone, coumarin, perylene, oxadiazole, polyenes, oligothiophenes, oligophenylenes, phenylene vinylenes, thiophene vinylenes and mixtures thereof. A more preferred organic dye component is 5,5'''-bis(aminoethyl)-2,2':5',2'':5'',2'''quaterthiophene (AEQT).

In order for a dye molecule to be suitable for incorporation in the organic-inorganic perovskite structure, several factors must be taken into account during its synthesis: a) One or two unobstructed ammonium units must be attached to the molecule, so that reasonably strong hydrogen bonding can occur between these groups and the perovskite sheet halogens. b) The cross-sectional area of the dye cation must fit within the area defined by the terminal halogens from four adjacent corner-sharing octahedra of the inorganic layers. Dyes with a long and narrow profile are preferable in this respect. The whole gamut of the visual spectrum can be covered by the use of different dyes, an important feature if full color display applications are to be realized.

In another embodiment of the present invention, a portion of the organic dye component in the organic-inorganic hybrid material is replaced with an optically inert material component. An optically inert component is one that does not absorb or fluoresce in the visible range. The incorporation of the optically inert material component may actually increase fluorescence because most dyes self quench in high concentrations. The dye concentration should be less than 70 mole %, preferably less than 50 mole %, more preferably less than 20 mole %, still more preferably less than 10 mole % and even more preferably less than 5 mole % based on the total organic component in the organic-inorganic hybrid material. Any suitable optically inert organic cation material may be used as long as it will bond to the inorganic component to preserve the predicable nature of the hybrid material. A preferred optically inert material is 1,6-bis(5'-(2"aminoethyl)-2'-thienyl) hexane (AETH). Other inert materials can be synthesized using similar design rules as those described above for the dye molecules with, however, the additional constraint that its optical absorption must lie at higher energies than that for the dye, to avoid energy transfer from the dye. Usually, such molecules can be very similar to the dye but modified so they do not emit light. This can be accomplished, for example, by breaking the conjugation (i.e. breaking the sequence of alternating double(or triple) and single bonds).

Besides altering the organic component, various modifications can be made to the inorganic component. Appropriate selection of the metal and halogen atoms change the location of the exciton arising in the inorganic sheet, which can be tuned to different areas of the optical spectrum. For example, with a perovskite of the formula $(RNH_3)_2PbX_4$, (R=alkyl), the exciton is located at 332, 405 and 504 nm when X is Cl, Br and I respectively. To obtain optimal fluorescence, the organic dye component is chosen to absorb in the energy range at which the exciton is located or at lower energy.

Likewise, a change in the inorganic sheet thickness can vary the conductance of the film. For example, for the $(C_4H_9NH_3)_2(CH_3NH_3)_{n-1}Sn_nI_{3n+1}$ perovskite family, the room temperature resistivity decreases with increasing sheet thickness, "n", yielding even a metallic character when n is higher than 3.

EXAMPLE 1

Figure 4:
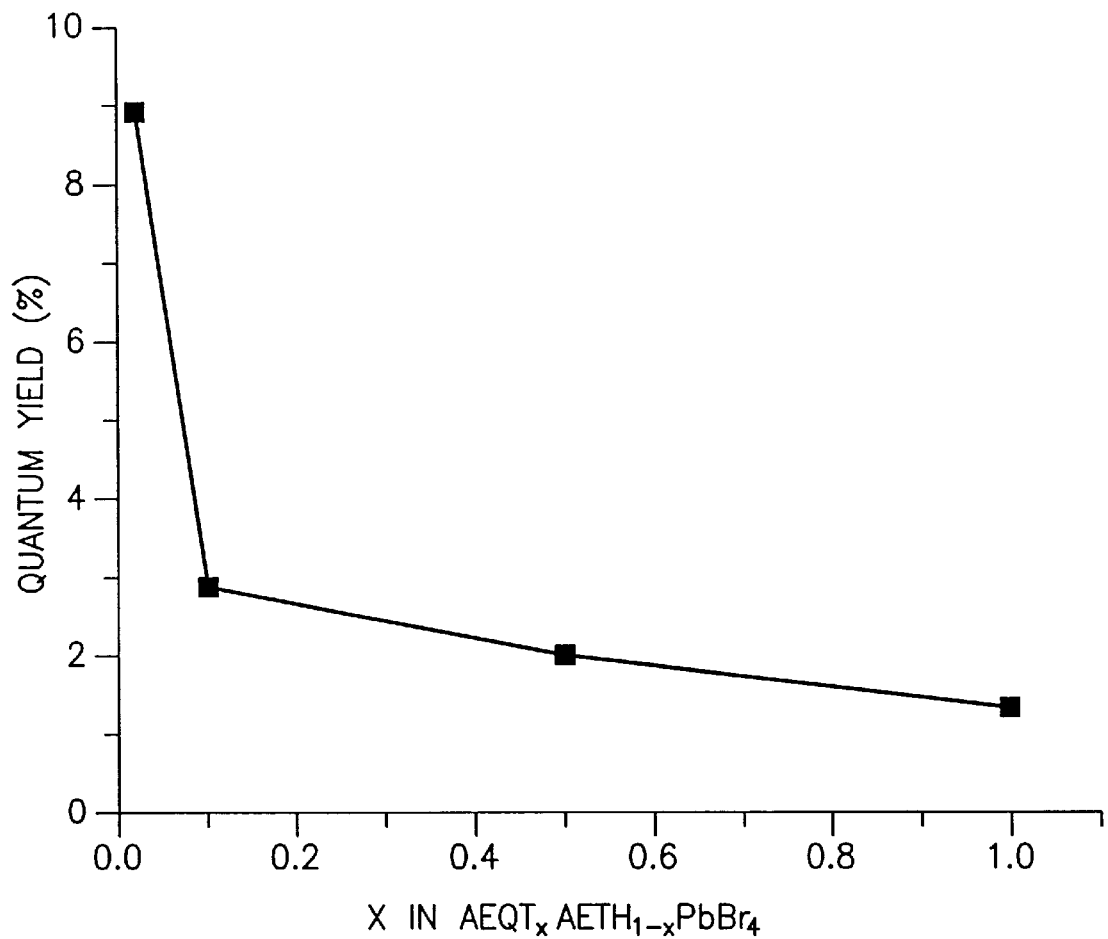
FIG. 4 is a plot of quantum yield vs. dye concentration for a material with the formula $AEQT_xAETH_{1-x}PbBr_4$.
Figure 5:
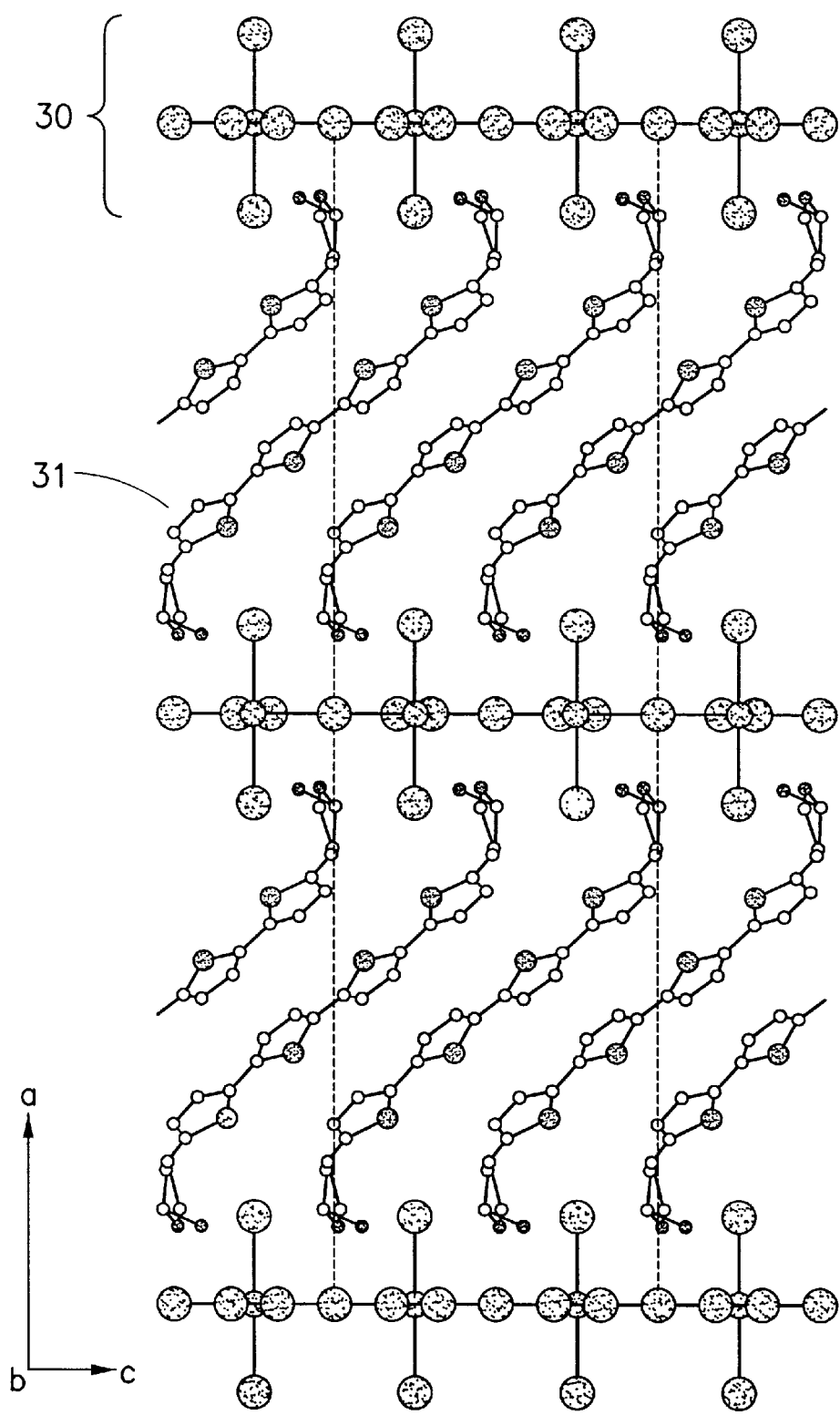
FIG. 5 is the structure of the compound $(AEQT)PbBr_4$ obtained from a single crystal x-ray structure determination.

To examine the approach of replacing a portion of the dye component with an optically inert material within an organic-inorganic hybrid, films with different ratios of the two organic components were prepared by thermal ablation. The organic dye component was AEQT and the optically inert material was AETH or bis(5'-(2"-aminoethyl)-2'-thienyl)hexane. The film material had the general formula $AEQT_xAETH_{1-x}PbBr_4$. Measurement of the photoluminescence quantum yield vs. dye concentration is shown in FIG. 4. The data reveals that there is a significant increase in quantum yield as the amount of dye relative to the inert material is decreased. The highest yield measured was when the concentration of the dye was approximately 2 mole %, which was the lowest concentration examined.

EXAMPLE 2

To examine the feasibility of incorporating AEQT in the perovskite structure without including the optically inert material, 0.025 mmol of AEQT was reacted with 0.025 mmol $PbBr_2$ in 30 ml of water acidified with 2 drops of concentrated HBr acid. The solution was heated at 110° C. and cooled slowly (−2° C.) at 2° C. Yellow sheetlike crystals of $(AEQT)PbBr_4$ were obtained after filtering the solution. The actual structure of the compound $(AEQT)PbBr_4$, obtained from a single-crystal X-ray determination, is shown in FIG. 6. The structure consists of two-dimensional $PbBr_4^{2-}$ layers 30 of corner-sharing $PbBr_6$ octahedra, which alternate with layers of diammonium organic cations 31. Strong ionic and hydrogen bonding between the organic and inorganic components give rise to a well-defined structure with a specific stoichiometry.

Deposition of the material as a thin film can be accomplished by various inexpensive, low temperature methods such as spin-coating, dip-coating or thermal evaporation. In this case a single-source, thermal ablation technique developed by ourselves (U.S. patent application 09/192,130) was employed for the deposition of thin films.

It should be noted that the foregoing description is only illustrative of the invention. Various alternatives and modifications can be devised by those skilled in the art without departing from the present invention.

What is claimed is:

1. An organic-inorganic hybrid material comprising an organic component and an inorganic component, wherein said organic component comprises a dye component that, upon excitation emits in a visible spectrum, mixed with an optically inert component that reduces interactions between dye molecules of said dye component and reduces quenching effects therebetween.

2. The material of claim 1, wherein said organic-inorganic hybrid material has an inorganic component consisting of a metal halide framework.

3. The material of claim 1, wherein said organic-inorganic hybrid material is a perovskite.

4. The material of claim 1 wherein said dye material fluoresces in the visible range.

5. The material of claim 3 wherein said perovskite has the general formula: $(RNH_3)_2(CH_3NH_3)_{n-1}M_nX_{3n+1}$, wherein R is an organic group; M is a divalent metal, X is a halogen and n is a number of perovskite sheets sandwiched between each bilayer of $RNH_3$ cations.

6. The material of claim 3 wherein said perovskite has the general formula: $(NH_3—R—NH_3)(CH_3NH_3)_{n-1}M_nX_{3n+1}$, wherein R is an organic group; M is a divalent metal, X is a halogen and n is a number of perovskite sheets sandwiched between each layer of $NH_3—R—NH_3$.

7. The material of claim 5 wherein M is a group IVA metal.

8. The material of claim 6 wherein M is a group IVA metal.

9. The material of claim 4 wherein said dye component is selected from the group consisting of derivatives of tolan, thioxanthone, coumarin, perylene, oxadiazole, polyenes, oligothiophenes, oligophenylenes, phenylene vinylenes, thiophene vinylenes and mixtures thereof.

10. The material of claim 4 wherein said dye component is 5 5,5'''-bis(aminoethyl)-2,2':5',2":5",2'''-quaterthiophene (AEQT).

11. The material of claim 9 wherein said dye component is greater than 0 and less than 10% of the total organic component.

12. The material of claim 9 wherein said dye component is greater than 0 and less than 5% of the total organic component.

13. The material of claim 1, wherein said inert material is selected from the group consisting of AETH, phenethylamine (PEA), butyl diamine (BDA), other alkyl amines, and modified (non-conjugated) dye molecule derivatives of tolan, thioxanthone, coumarin, perylene, oxadiazole, polyenes, oligothiophenes, oligophenylenes, phenylene vinylenes, thiophene vinylenes.

14. A perovskite material comprising an organic component and an inorganic component, wherein said organic component comprises a dye component that fluoresces in the visible range, wherein said dye component is 5,5'''-bis(aminoethyl)-2,2':5',2":5",2'''-quaterthiophene (AEQT).

* * * * *